United States Patent [19]

McCulloch

[11] Patent Number: 4,876,390
[45] Date of Patent: Oct. 24, 1989

[54] PROCESS FOR SEPARATING DICHLORODIPHENYLSULFONE ISOMERS

[75] Inventor: Beth McCulloch, Barrington, Ill.

[73] Assignee: UOP, Des Plaines, Ill.

[21] Appl. No.: 233,706

[22] Filed: Aug. 19, 1988

[51] Int. Cl.$^4$ .............................................. C07C 147/06
[52] U.S. Cl. ........................................ 568/34; 210/674
[58] Field of Search ........................... 210/674; 568/34

[56] References Cited

U.S. PATENT DOCUMENTS

| | | | |
|---|---|---|---|
| 2,882,244 | 4/1959 | Milton | 252/455 |
| 2,985,589 | 5/1961 | Broughton et al. | 210/34 |
| 3,040,777 | 6/1962 | Carson et al. | 137/625.15 |
| 3,130,007 | 4/1964 | Breck | 23/113 |
| 3,265,750 | 8/1966 | Peck et al. | 260/666 |
| 3,309,409 | 3/1967 | Steiger | 260/607 |
| 3,334,146 | 8/1967 | Pitt et al. | 260/607 |
| 3,422,848 | 1/1969 | Liebman et al. | 137/625.15 |
| 3,706,812 | 12/1972 | DeRosset et al. | 260/674 SA |
| 4,012,451 | 3/1977 | Enoki et al. | 568/34 |
| 4,024,331 | 5/1977 | Neuzil et al. | 536/1 |
| 4,642,397 | 2/1987 | Zinnen et al. | 568/934 |

Primary Examiner—Mary E. Ceperley
Attorney, Agent, or Firm—Thomas K. McBride; John F. Spears, Jr.; Jack H. Hall

[57] ABSTRACT

A process for the liquid phase adsorptive separation of 4,4'-dichlorodiphenylsulfone (4,4'-DCDPS) from crystallization residue feed mixture also containing other DCDPS isomers. The feed is contacted with an X or Y type zeolite, substituted with a cation of a Group IA or IIA metal or ammonium. The other isomers are selectively adsorbed to the substantial exclusion of 4,4'-DCDPS. The 4,4'-DCDPS is recovered in high purity by fractionating the raffinate to recover the desorbent, aliphatic alcohols having 4–8 carbon atoms either used alone or diluted with an aromatic compound.

9 Claims, No Drawings

PROCESS FOR SEPARATING DICHLORODIPHENYLSULFONE ISOMERS

BACKGROUND OF THE INVENTION

1. Field of the Invention

The field of art to which this invention pertains is the solid bed adsorptive separation of dichlorodiphenylsulfone (DCDPS) isomers. More specifically, the invention relates to a process for separating 4,4'-DCDPS mixture comprising 4,4'-DCDPS and one or more additional DCDPS isomers, which process employs an adsorbent comprising a crystalline aluminosilicate to selectively adsorb all isomers except 4,4'-DCDPS from the feed mixture and remove 4,4'-DCDPS as the product in the raffinate.

2. Description of the Prior Art

The use of crystalline aluminosilicates to perform a number of separations is well known in the separation art. Examples of such separations are the use of zeolites to separate normal paraffins from branched chain paraffins, (U.S. Pat. No. 2,985,589), faujasites to separate olefinic hydrocarbons from paraffinic hydrocarbons (U.S. Pat. No. 3,265,750), zeolites to separate specific monosaccharides or classes of monosaccharides from carbohydrate feed mixtures (U.S. Pat. No. 4,024,331), etc.

This invention is particularly concerned with the separation of 4,4'-DCDPS from other isomers of DCDPS. Obtaining pure 4,4'-DCDPS has commercial significance in light of its potential as a monomer or co-monomer for the production of polysulfone resins, polyethersulfone resins, polyarylsulfone resins, etc. A source of the isomer mixture is the sulfonation of chlorobenzene with $SO_3$ and thionylchloride or through a series of well-known reactions or the reaction of dimethylpyrosulfate with monochlorobenzene, both of which produce a mixture of DCDPS isomers. It is desirable to use very pure 4,4'-isomer as the polymerization reactant. Typically, however, the initial purification is by crystallization, which can recover about 60% of the 4,4'-isomer, but a means must be found to economically recover 4,4'-DCDPS in concentrations greater than about 90–95%, and, ideally, greater than 98% in order to manufacture high quality polysulfone resins. Recrystallization is effective for the concentration proposed, but more costly than a chromatographic adsorptive separation.

Current methods of separating DCDPS isomers include filtration of isomer reaction mixture following precipitation with a basic aqueous solution (U.S. Pat. No. 3,309,409) and crystallization with monochlorobenzene as solvent (U.S. Pat. No. 3,334,146).

While crystalline aluminosilicates or zeolites have been used in adsorption separations of various mixtures in the form of agglomerates having high physical strength and attrition resistance, to our knowledge an effective chromatographic separation process for DCDPS isomers has not been found. Methods for forming the crystalline powders into agglomerates are also known and include the addition of an inorganic binder, generally a clay comprising a silicon dioxide and aluminum oxide, to a high purity zeolite powder in wet mixture. The blended clay zeolite mixture is extruded into cylindrical type pellets or formed into beads which are subsequently calcined in order to convert the clay to an amorphous binder of considerable mechanical strength. As binders, clays of the kaolin type, water permeable organic polymers or silica are generally used.

The invention herein can be practiced in fixed or moving adsorbent bed systems, but the preferred system for this separation is a countercurrent simulated moving bed system, such as described in Broughton U.S. Pat. No. 2,985,589, incorporated herein by reference. Cyclic advancement of the input and output streams can be accomplished by a manifolding system, which are also known, e.g., by rotary disc valves shown in U.S. Pat. Nos. 3,040,777 and 3,422,848. Equipment utilizing these principles are familiar, in sizes ranging from pilot plant scale (deRossett U.S. Pat. No. 3,706,812) to commercial scale in flow rates from a few cc per hour to many thousands of gallons per hour.

The functions and properties of adsorbents and desorbents in the chromatographic separation of liquid components are well-known, but for reference thereto, Zinnen et al. U.S. Pat. No. 4,642,397 is incorporated herein.

It has now been discovered that X- or Y-type zeolites exchanged with cations at cation exchange sites selected from Groups IA or IIA are suitable adsorbents for the separation of 4,4'-DCDPS from other isomers of DCDPS, provided certain conditions in the chromatographic separation process are maintained. Important parameters to be controlled in the process are water concentration of the adsorbent, temperature of the process and concentration of desorbent components. Moreover, by our process, it is estimated that 4,4'-DCDPS can be obtained at purities of at least 95% to as high as 99+% with recoveries at 90–99%.

SUMMARY OF THE INVENTION

It is accordingly a broad objective of the present invention to provide a process for the separation of 4,4'-DCDPS from a feed mixture containing DCDPS isomers using an X or Y type zeolite with cations selected from Group IA, Group IIA or ammonium ions at cation exchanged sites. Especially preferred are Na, K, Ca and Ba.

In brief summary, the present invention is a process for separating 4,4'-DCDPS from a feed mixture comprising 4,4'-DCDPS and at least one other DCDPS isomer. The process comprises contacting, at adsorption conditions, the DCDPS isomer mixture with an adsorbent comprising a type X zeolite or type Y zeolite containing Group IA or IIA cations or ammonium ions at the exchangeable cationic sites, selectively adsorbing 2,4'- and 3,4'-DCDPS to the substantial exclusion of 4,4'-DCDPS, removing the nonadsorbed 4,4'-DCDPS from contact with the adsorbent as product raffinate and thereafter removing the remaining isomers by desorption at desorption conditions. Adsorption conditions which are important to the economic recovery of 4,4'-DCDPS are: adsorption and desorption temperatures of at least 150° C. and water concentration on the adsorbent of 1–7 wt.%. The desorbent comprises from 20–100% $C_4$–$C_8$ alcohol mixed with 0–80% of an aromatic diluent, e.g., toluene, benzene, xylene, mesitylene, chlorobenzene, chlorotoluene, etc.

DETAILED DESCRIPTION OF THE INVENTION

Adsorbents to be used in the process of this invention will comprise specific crystalline aluminosilicates or molecular sieves, namely X and Y zeolites. The zeolites have known cage structures in which the alumina and silica tetrahedra are intimately connected in an open three dimensional network to form cage-like structures with window-like pores. The tetrahedra are cross-linked by the sharing of oxygen atoms with spaces between the tetrahedra occupied by water molecules prior to partial or total dehydration of this zeolite. The dehydration of the zeolite results in crystals interlaced with cells having molecular dimensions and thus the crystalline aluminosilicates are often referred to as "molecular sieves."

In hydrated form, the X and Y zeolites used in the process of this invention have the structure described and defined in U.S. Pat. Nos. 2,882,244 and 3,130,007, respectively, incorporated herein by reference thereto. The X or Y zeolites in the hydrated or partially hydrated form can be represented in terms of moles of metal oxides as shown, respectively, by Formulas 1 and 2 below:

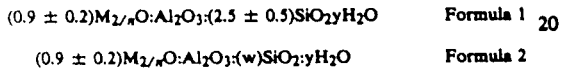

$(0.9 \pm 0.2)M_{2/n}O:Al_2O_3:(2.5 \pm 0.5)SiO_2 yH_2O$  Formula 1

$(0.9 \pm 0.2)M_{2/n}O:Al_2O_3:(w)SiO_2:yH_2O$  Formula 2 where "M" is at least one cation having a valence not more than 3, "n" represents the valence of "M", "w" is a value from 3 to 6 and "y", representing the number of moles of water, is a value up to about 9 depending upon the identity of "M" and the degree of hydration of the crystal. The cation "M", as the zeolite is initially prepared, is usually predominately sodium, but for the purpose of this invention, the sodium may be replaced with calcium, barium, or potassium cations by ion exchange methods well known to those having ordinary skill in the field of crystalline aluminosilicates. Such methods are generally performed by contacting the zeolite or an adsorbent material containing the zeolite with an aqueous solution of the soluble salt of the cation or cations desired to be placed upon the zeolite. After the desired degree of exchange takes place, the sieves are removed from the aqueous solution, washed, and dried to a desired water content.

The adsorbent may be supported by an inorganic matrix material such as silica, titania, or alumina or mixtures thereof, or compounds, such as clays, which material is present in intimate mixture with the small particles of the zeolite material. This matrix material, or binders, typically in amounts ranging from 2-25 wt.%, aids in forming or agglomerating the particles and may be an adjunct of the manufacturing process for zeolite, (for example, intentionally incomplete purification of either zeolite during its manufacture) or it may be added to relatively pure zeolite. Normally, the adsorbent will be in the form of particles such as extrudates, aggregates, tablets, macrospheres or granules having a desired particle size range. The typical adsorbent will have a particle size range of about 16-60 mesh (Standard U.S. Mesh).

Although it is not clear what properties of the adsorbent are responsible for the DCDPS separation herein described, it appears that it cannot be attributed to pore size selectivity alone. Since the isomers being separated are of similar size, it appears that steric factors as well as electrostatic attraction action may play an important role in the separation. while it is not possible to conclusively set forth the molecular interaction responsible for the adsorption, one possible explanation is higher polarity of the minor isomers compared to that of the 4,4'-isomers. Therefore, both electrostatic interaction as well as physical considerations may provide the mechanism for this separation.

We have found that either X or Y zeolites with sodium, potassium, calcium or barium cations and amorphous binders possess the selectivity and other necessary requirements for use in our process; however, a potassium exchanged Y type zeolite is particularly preferred, because it is also possible to use the same desorbent in a second pass to separate the two extract components, 2,4'-DCDPS in a second stage, with especially advantageous results at a temperature of 180° C.

In this process, and particularly the preferred continuous simulated moving bed process, the desorbent must be selected to satisfy the following criteria: First, the desorbent material should displace an extract component from the adsorbent with reasonable mass flow rates without itself being so strongly adsorbed as to unduly prevent an extract component from displacing the desorbent material in a following adsorption cycle. Secondly, the desorbent material must be compatible with the particular adsorbent and the particular feed mixture. More specifically, it must not reduce or destroy the critical selectivity of the adsorbent for an extract component with respect to a raffinate component. The desorbent should additionally be easily separable from the feed mixture that is passed into the process. Both the raffinate stream and the extract stream are removed from the adsorbent in admixture with desorbent material and without a method of separating at least a portion of the desorbent material, the purity of the extract product and the raffinate product would not be very high nor would the desorbent material be available for reuse in the process. It is, therefore, contemplated that any desorbent material used in this process will preferably have a substantially different average boiling point than that of the feed mixture, i.e., more than about 5° C. difference, to allow separation of at least a portion of desorbent material from feed components in the extract and raffinate streams by simple fractional distillation, thereby permitting reuse of desorbent material in the process. Finally, desorbent materials should also be materials which are readily available and, therefore, reasonable in cost. However, a suitable desorbent or desorbents for a particular separation with a specific adsorbent are not always predictable. In the preferred isothermal, isobaric, liquid-phase operation of the process of my invention, I have found that desorbent material comprising an alcohol having 4 to 8 carbon atoms will result in selectivity for the adsorbed DCDPS isomers when used with the above discussed adsorbents. The combination of KX or KY adsorbent and pentanol diluted with about 0-80 wt.% toluene was found to be most effective in separating the DCDPS isomers.

Feed mixtures which can be utilized in the process of this invention will comprise a mixture of at least two isomers of DCDPS, which have the structure:

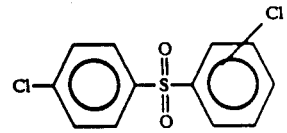

Potential feed mixtures containing substantial quantities of 4,4'-DCDPS will typically contain 2,4'- and 3,4'-DCDPS as well. Such mixtures may also contain significant quantities of other impurities. A typical feed mixture for this invention is a crystallization residue of the crude reaction mixture and will contain from 51–75%, 4,4'-DCDPS, 21–37.6%, 2,4'-DCDPS and 4–11.0% (by wt.) 3,4'-DCDPS. The invention is applicable to other feed mixtures, including crude reaction products containing approximately 95–98% 4,4'-DCDPS, 1–2% 3,4'-DCDPS and 1–4% 2,4'-DCDPS.

Although both liquid and vapor phase operations can be used in many adsorptive separation processes, liquid-phase operation is preferred for this process because of the lower temperature requirements and because of the higher yields of extract product that can be obtained with liquid-phase operation over those obtained with vapor-phase operation. Adsorption conditions will include a temperature range of from about 20° to about 200° C. with about 100° to about 180° C. being more preferred and a pressure sufficient to maintain liquid phase, ranging from about atmospheric to about 500 psig with from about atmospheric to about 25 psig being preferred. Desorption conditions will include the same range of temperatures and pressures as used for adsorption conditions.

At least a portion of the raffinate stream, which contains the concentrated 4,4'-DCDPS product, and preferably at least a portion of the extract stream, from the separation process are passed to separation means, typically fractionators or evaporators, where at least a portion of desorbent material is separated to produce a raffinate product and an extract product, respectively.

A static test procedure and apparatus may be employed to test various adsorbents with a particular feed mixture to determine the relative retention by the adsorbent of each component of the mixture. The procedure involves mixing together equal quantities of each component, the relative retention of which is to be determined, and a convenient solvent or desorbent material. A solvent or desorbent is selected that will have a boiling point well separated from those of the isomers being tested. The resulting solution is then placed in a vessel with a quantity of the appropriate adsorbent and is allowed to remain, with occasional stirring, overnight at room temperature. The solution is then analyzed for each component and the selectivity, alpha, thereof is calculated from the following equation:

$$Alpha_{4,4'/2,4'} = \text{Amount adsorbed, 4,4'-/Amount unadsorbed, 4,4'-} \div \text{Amount adsorbed, 2,4'-/Amount unadsorbed, 2,4'-}.$$

A dynamic testing apparatus is employed to test various adsorbents with a particular feed mixture and desorbent material to measure the adsorption characteristics of retention capacity and exchange rate. The apparatus consists of a helical adsorbent chamber of approximately 70 cc volume having inlet and outlet portions at opposite ends of the chamber. The chamber is contained within a temperature control means and, in addition, pressure control equipment is used to operate the chamber at a constant predetermined pressure. Quantitative and qualitative analytical equipment such as refractometers, polarimeters and chromatographs can be attached to the outlet line of the chamber and used to detect quantitatively or determine qualitatively one or more components in the effluent stream leaving the adsorbent chamber. A pulse test, performed using this apparatus and the following general procedure, is used to determine data, e.g., selectively, for various adsorbent systems. The adsorbent is placed in a chamber and filled to equilibrium with a particular desorbent material by passing the desorbent material through the adsorbent chamber. At a convenient time, a pulse of feed containing known concentrations of a tracer and of a particular extract component or of a raffinate component or both, all diluted in desorbent material is injected for a duration of several minutes. Desorbent material flow is resumed, and the tracer and the extract component or the raffinate component (or both) are eluted as in a liquid-solid chromatographic operation. The effluent can be analyzed on-stream or alternatively, effluent samples can be collected periodically and later analyzed separately by analytical equipment and traces of the envelopes or corresponding component peaks developed.

From information derived from the test, adsorbent performance can be rated in terms of void volume, retention volume for an extract or a raffinate component, the rate of desorption of an extract component from the adsorbent and selectivity. The retention volume of an extract or a raffinate component may be characterized by the distance between the center of the peak envelope of the extract or raffinate component and the center of the peak envelope of the tracer component (void volume) or some other known reference point. It is expressed in terms of the volume in cubic centimeters of desorbent material pumped during this time interval represented by the distance between the peak envelopes. The rate of exchange or desorption rate of an extract component with the desorbent material can generally be characterized by the width of the peak envelopes at half intensity. The narrower the peak width, the faster the desorption rate. [The desorption rate can also be characterized by the distance between the center of the tracer peak envelope and the disappearance of an extract component which has just been desorbed. This distance is again the volume of desorbent material pumped during this time interval.] Selectivity, $\beta$, is determined by the ratio of the net retention volumes of the more strongly adsorbed component to each of the other components.

The examples shown below are intended to further illustrate the process of this invention without unduly limiting the scope and spirit of said process. The examples present test results for various adsorbent and desorbent materials when using the above dynamic testing apparatus.

EXAMPLE I

A number of static tests were performed as described hereinabove at 25° C. to demonstrate that it was possible to separate the isomers by an adsorptive process. The feed consisted of 1 or 3% crystallizer residue in mesitylene or toluene; the crystallizer residue contained 58.7% 4,4'-DCDPS; 3.4% 3,4'-DCDPS and 16.5% 2,4'-DCDPS. Values for alpha of 4,4'-DCDPS with respect to 2,4'-DCDPS, a measure of selectivity, calculated as stated above for a number of adsorbents, are listed in Table 1.

TABLE 1

| | $Alpha_{4,4'-/2,4'}$-DCDPS | | |
|---|---|---|---|
| | Mesitylene | Toluene | |
| Adsorbent | 3% feed | 1% feed | 3% feed |
| NaX | 0.69 | 0.81 | — |
| KX | 0.56 | 0.35 | 0.48 |
| BaX | 0.89 | 0.72 | 0.69 |
| NH4X | 0.49 | 0.40 | 0.57 |
| NaY | 0.84 | 0.57 | 0.78 |
| CaY | 0.67 | 0.76 | 0.67 |

TABLE 1-continued

| | Alpha 4,4'-/2,4'-DCDPS | | |
|---|---|---|---|
| | Mesitylene | Toluene | |
| Adsorbent | 3% feed | 1% feed | 3% feed |
| KY | 0.75 | — | 0.53 |

EXAMPLE II

In this example, a pulse test, as described, was run at 150° C. using a Y type zeolite having potassium ions at cation exchange sites to determine the rejective separation of 4,4'-dichlorodiphenylsulfone from a crystallizer residue. The K-Y zeolite of this example was bound with bentonite clay and had an average bulk density of 0.56 gm/ml. The feed mixture consisted of 3 g of the crystallizer residue composition given in Table 2 diluted with 97 g of the desorbent. The 4,4'-dichlorodiphenylsulfone was removed as raffinate from the column. The 2,4'-DCDPS and 3,4'-DCDPS isomers were desorbed with 100% pentanol and recovered as extract.

TABLE 2

| Component | Wt. % |
|---|---|
| 4,4'-DCDPS | 51.4 |
| 2,4'-DCDPS | 37.6 |
| 3,4'-DCDPS | 11.0 |
| | 100.0 |

EXAMPLES III-IX

Examples III through IX were also pulse tests run to illustrate the invention using other adsorbents, desorbents and diluents and temperatures. In each case, except Example IX, the feed, 15 g of a crystallizer residue composition given in Table 4, is diluted with 85 g of the desorbent.

TABLE 4

| Component | Wt. % |
|---|---|
| 4,4'-DCDPS | 51.4 |
| 2,4'-DCDPS | 37.6 |
| 3,4'-DCDPS | 11.0 |

In Example IX, the feed, 8 g of a crude mixture, having the composition of Table 5, obtained from the reaction of dimethylpyrosulfate and monochlorobenzene, is diluted with 92 g of the desorbent.

TABLE 5

| Component | Wt. % |
|---|---|
| 4,4'-DCDPS | 96.91 |
| 3,4'-DCDPS | 1.00 |
| 2,4'-DCDPS | 2.09 |

The results for each example are set forth in Table 6.

TABLE 6

| EX. | Adsorbent | Desorbent | Temp. (°C.) | Retention Volume (Width at ½ Peak Height) | | | | Selectivity $\beta_{4,4'-/( )}$ |
|---|---|---|---|---|---|---|---|---|
| | | | | 4,4'- | 2,4'- | 3,4'- | Other | |
| III | K-Y | 20/70 pentanol/ toluene | 150 | 45.3 (6.24) | 70.7 (16.13) | 55.1 (9.55) | 41.8 (7.86) (unknown) | 0.12 (2,4'-) 0.26 (3,4'-) |
| IV | K-Y | 30/70 pentanol/ toluene | 150 | 44.6 (9.28) | 58.7 (16.5) | 52.9 (11.13) | 42.4 (6.54) (unknown) | 0.14 (2,4'-) 0.21 (3,4'-) |
| V | K-Y | 50/50 pentanol/ toluene | 150 | 44.5 (9.51) | 53.7 (13.08) | 49.2 (9.25) | 41.4 (5.03) (unknown) | 0.25 (2,4'-) 0.40 (3,4'-) |
| VI | K-Y (aged) | 30/70 pentanol toluene | 150 | 46.5 (12.35) | 67.7 (7.58) | N/A — | — | 0.18 (2,4'-) — |
| VII | K-Y | 30/70 pentanol/ toluene | 180 | 43.8 (9.07) | 70.0 (18.31) | 56.7 (11.59) | 40.1 (5.82) (unknown) | 0.12 (2,4'-) 0.22 (3,4'-) |
| VIII | K-Y | 67/33 n-octanol toluene | 150 | 52.3 (9.88) | 86.7 (32.78) | 62.9 (7.86) | — | 0.22 (2,4'-) 0.48 (3,4'-) |
| IX | K-Y | 30/70 pentanol/ toluene | 150 | 45.5 (8.12) | 57.2 (15.21) | 51.6 (8.06) | — | 0.21 (2,4'-) 0.34 (3,4'-) |

Table 3 shows the results of the separation as demonstrated by the net retention volumes of the components.

TABLE 3

| Component | Adsorbent | Desorbent | Net Retention Vol. (NRV) | Width at ½ Ht. | Selectivity (Beta) |
|---|---|---|---|---|---|
| 4,4'-DCDPS | KY | Pentanol | 1.5 | 9.99 | 4.80 |
| 2,4'-DCDPS | | | 7.2 | 11.70 | 1.00 |
| 3,4'-DCDPS | | | 4.2 | 9.74 | 1.75 |
| Other (Unknown, etc.) | | | 1.5 | 5.02 | 4.80 |

It will be noted that many of the separations provide sufficient selectivity between the extract products, 2,4'-DCDPS and 3,4'-DCDPS, that these isomers could be separated in a second stage operation using these particular adsorbent-desorbent combinations, e.g., KY-n-octanol/toluene as in Example VIII.

What is claimed is:

1. A process for separating an isomer of dichlorodiphenylsulfone from a feed mixture containing 4,4'-dichlorodiphenylsulfone and at least one other isomer thereof, which comprises contacting at adsorption conditions said mixture with an adsorbent comprising a type Y or type X zeolite having cations selected from Group IA or IIA metals and ammonium at exchangeable cation sites, adsorbing said other isomers to the substantial exclusion of said 4,4'-dichlorodiphenylsulfone, removing the nonadsorbed 4,4'-dichlorodiphenylsulfone from contact with said adsorbent as raffinate product and thereafter desorbing said other isomers by desorption at desorption conditions with a desorbent comprising an aliphatic alcohol having 4–8 carbon atoms.

2. The process of claim 1 wherein said other isomers are selected from the group consisting of 2,4'-dichlorodiphenylsulfone and 3,4'-dichlorodiphenylsulfone and mixtures thereof.

3. The process of claim 1 wherein said desorption conditions comprise temperature within the range of 150°–180° C. and wherein said adsorbent comprises 1 to 7% water.

4. The process of claim 1 wherein the desorbent is selected from the group consisting of pentanol and a mixture of pentanol and toluene.

5. The process of claim 4 wherein said desorbent comprises a mixture of 50–70% pentanol and 50–30% toluene.

6. The process of claim 1 wherein said adsorbent comprises a type Y adsorbent cation-exchanged with potassium and said desorbent comprises 30% pentanol and 70% toluene.

7. The process of claim 1 wherein said separation is effected by means of a countercurrent flow, simulated moving bed flow scheme.

8. A process for separating an isomer of dichlorodiphenylsulfone from a feed mixture containing at least two isomers thereof, which comprises contacting at adsorption conditions said mixture with an adsorbent comprising a type Y or type X zeolite having cations selected from Group IA or IIA metals and ammonium at exchangeable cation sites, adsorbing one of said isomers to the substantial exclusion of said other isomers, removing the nonadsorbed isomer from contact with said adsorbent as raffinate product and thereafter desorbing said one isomer by desorption at desorption conditions with a desorbent comprising an aliphatic alcohol having 4–8 carbon atoms.

9. The process of claim 8 wherein said adsorbed isomer is 2,4'-DCDPS and said nonadsorbed isomer is 3,4'-DCDPS.

* * * * *